United States Patent [19]
Bast et al.

[11] Patent Number: 5,647,667
[45] Date of Patent: Jul. 15, 1997

[54] PROOF TEST FOR CERAMIC PARTS

[75] Inventors: Ulrich Bast; Karl Kempter, both of Munich; Thomas Schulenberg, Essen, all of Germany

[73] Assignee: Siemsns Aktiengesellschaft, Munich, Germany

[21] Appl. No.: 479,079

[22] Filed: Jun. 6, 1995

[30] Foreign Application Priority Data

Jun. 6, 1994 [DE] Germany .................. 44 19 750.0

[51] Int. Cl.$^6$ .................... G01N 3/60; G01N 25/00
[52] U.S. Cl. .................... 374/57; 73/643
[58] Field of Search ................ 374/57; 73/587, 73/787, 601, 598, 600

[56] References Cited

U.S. PATENT DOCUMENTS

| | | | |
|---|---|---|---|
| 3,534,597 | 10/1970 | Webb | 374/57 |
| 3,924,466 | 12/1975 | Vahaviolos | 73/770 |
| 4,277,977 | 7/1981 | Lubitz et al. | 73/587 |
| 4,593,565 | 6/1986 | Chamuel | 73/643 |
| 4,710,030 | 12/1987 | Taue et al. | 374/57 |
| 4,752,140 | 6/1988 | Cielo et al. | 374/57 |
| 4,793,716 | 12/1988 | Wei et al. | 374/57 |
| 4,914,952 | 4/1990 | Miyajima et al. | 73/600 |
| 4,972,720 | 11/1990 | Wu | 374/57 |
| 5,457,997 | 10/1995 | Narou et al. | 73/643 |
| 5,567,051 | 10/1996 | Annati et al. | 374/57 |

FOREIGN PATENT DOCUMENTS 42 01 943 A1  7/1993  Germany .

OTHER PUBLICATIONS

Thermal Shock Resistance of Ceramics Determined by Acoustic Emission Analysis, Esper et al, Dec. 1978, No. 12, 507–510.

Primary Examiner—Thomas B. Will
Attorney, Agent, or Firm—Hill, Steadman & Simpson

[57] ABSTRACT

For testing structural ceramic parts under overload conditions, a previously calculated temperature distribution is generated on the part by thermal radiation, this temperature distribution inducing the desired test stress or overload. The temperature distribution is measured with topically and temporally resolving temperature sensors, is compared to a desired or calculated temperature distribution, and is regulated by varying the duration and/or location of the radiation influence until the desired temperature distribution has been produced.

10 Claims, 1 Drawing Sheet

PROOF TEST FOR CERAMIC PARTS

BACKGROUND OF THE INVENTION

The high strength achieved by ceramic materials such as, for example, silicon nitride or silicon carbide allows the employment of these materials for structural applications, for example for heat shields or turbine paddles. By contrast to metallic materials, the ceramics retain their high strength up to temperatures far above 1000° C. This and the high resistance to corrosion open up various applications for the ceramic as a construction material, particularly in the high-temperature range.

Technical concepts that hitherto ran afoul of the lack of suitable materials can be realized by employing ceramic. The goal of these concepts is usually lower exhaust gas emissions and saving fuel. One example of this is achieving higher efficiencies in vehicular and stationary gas turbines by increasing the operating temperature. A further example is a lower-loss and quieter drive in ceramic admission and discharge valves of piston motors by reducing the friction and the oscillating masses.

However, problems can also arise given the employment of ceramic parts, these being caused by disadvantages such as brittleness and scatter of the mechanical properties that are typical of ceramics. Ceramics can exhibit manufacture-conditioned errors such as microcracks, pores, agglomerates, etc. These can lead to a local stress elevation under thermally and mechanically loaded operating conditions that cannot be relieved in the ceramic by plastic deformation, but only by the formation and growth of cracks. When the critical load is exceeded, this leads to the failure of the part.

Since these structural faults typical of ceramics occur in a statistical distribution with respect to their frequency, shape and size, the realizability of ceramic parts can only be enhanced when all parts that contain faults above a specific fault magnitude are eliminated by a proof test before their intended use or before integration. In a proof test, all parts are loaded with a test stress that is greater than the maximum stress occurring during operation The magnitude of the test stress is dependent on the maximum use stress and on the desired service life. The latter is in tun likewise dependent on the initial crack length from which, given a known sub-critical crack growth, the time until a critical crack size is reached can be calculated.

The load conditions that occur during operation should be simulated as exactly as possible in the proof test. Particularly given parts wherein the operating stresses are mainly produced by temperature gradients the stress distribution, however, can usually not be produced by purely mechanical testing without having highly elevated stresses arising at locations that are less loaded during operation. This would result in a great number of breakages during the overload test.

Different applications of ceramic parts can produce different part geometries and different load conditions. There is therefore no standard method for an overload lest. Specific overload tests already exist for individual applications. For example, ceramic balls for hip joint prostheses can be tested by a defined impression of a cone into the receptacle bore for the shaft.

Turbo-supercharger rotors and paddle wheels of vehicle gas turbines can be subjected to a test with excess rpm in the cold condition before being built in. Ceramic grinding wheels are also tested in this way. What is disadvantageous about this method is that thermal stresses and vibrations are not taken into consideration, and that it is limited to rotationally symmetrical parts.

An attempt, for example, is made with the assistance of the thermal shock method to simulate the loads during operation induced by thermal stresses. The parts are thereby heated by gas burners. The stresses produced in this way are calculated from the measured temperature distribution. With this method, however, the failure probability of ceramic parts dazing the operation thereof can be only slightly improved. The suspected reason for this is that the temperature distribution cannot be controlled when heating with the burner. As a result thereof, the stress generated in this way does not coincide with the conditions during the intended operation of the part. It is also possible that not all parts of the part to be tested are subjected to a test stress during the check test that exceeds the usual operating stress.

SUMMARY OF THE INVENTION

It is therefore an object of the present invention to specify a method for testing ceramic parts with which operation-specific test stresses can be generated in the ceramic part, which is simple to implement, and with which faulty parts can be just as reliably eliminated as parts comprising crack lengths lying above a limit value.

According to a method of the invention for testing a structural ceramic part by creating a thermally induced test stress, the part is heated by radiation action in predetermined regions. A temperature distribution of the part is then identified by topically resolving temperature sensors. The measured temperature distribution of the part is compared to a calculated, desired temperature distribution. Duration and/or location of the radiation action is regulated until the desired temperature distribution has been produced in the part. Failure of the part is detected by sound emission analysis.

The inventive method makes it possible to exactly generate that temperature distribution on the component part by the influence of radiation that generates the desired test stress. This is achieved, on the one hand, by the type of energy transmission (by the influence of thermal radiation) and, on the other hand, by the proposed control of the invention.

Adequate energy in order to generate the desired temperatures, which can lie above 1000° C., can be coupled into the ceramic part in the shortest possible time under the influence of radiation. On the other hand, the radiation can be arbitrarily bundled, so that the energy can be coupled in to the smallest space with high local precision. The energy in-feed is thus dearly faster than the thermal conduction, which leads to temperature balancing and thus to falsification of the desired temperature distribution.

Topically resolving temperature sensors are provided for controlling or regulating the method, these identifying the temperature of the part with optimum precision at a plurality of specific points. The temperature distribution measured in this way is compared to a desired, calculated temperature distribution and is matched to the desired temperature distribution on the basis of an appropriate influencing of the radiation source. Comparison and control of the temperature distribution can occur in a simple control circuit. It is also possible to control this via a computer.

Dependent on the size of the ceramic part to be tested and on the heat capacity connected therewith, a fast temperature sensor can also be necessary in order to permit an exact temperature regulation.

Lasers are particularly suited as radiation sources. However, it is also possible to employ halogen lamps, arc lamps and the like individually or in combination.

The desired temperature distribution occurs in a defined way by the temporal and topical control of the radiation action. In addition to comprising the duration of the action, the temporal control can also comprise an influencing of the pulse rate of the radiation.

Since both topical and temporal action of the radiation can be exactly set, the method can be adapted to part geometries that can be varied within broad limits.

Extreme temperature distributions or temperature distributions having a high temperature gradient can also be promoted by active cooling of the component at suitable locations.

A topical variation of the radiation action given employment of a laser can be undertaken, for example, by deflection of the laser beam with the assistance of two computer-controlled oscillating mirrors. The axes of the oscillating mirrors should be positioned perpendicularly relative to one another, so that hot zones having a complicated shape and temperature gradients selectable within broad limits can also be generated at the part under test. Greater topical excursions of the radiation action are generated by relative motion between radiation source and part. For example, the laser can be arranged immobile for this purpose, whereas the component part is secured on a planar table which, for example, can be moved along two axes perpendicular relative to one another with the assistance of stepping motors.

Given parts having a simple geometry and, particularly, given small parts under test, it is also possible to continuously or quasi-continuously conduct these past the radiation source with a suitable conveyor means. In this way, for example, function-ceramic parts can also be tested.

A structural ceramic part can be exposed to a plurality of different stress fields during its intended use. In the proof test of the invention, such different stress fields are also simulated by different temperature distributions. After generating a first temperature distribution in the component part, the latter is again cooled and is subsequently subjected to a different temperature distribution by renewed radiation action at a different location or with a different temperature gradient, and thus a different test stress is generated.

The curve of a desired temperature distribution or the position of the gradient of the temperature distribution can, for example, lie on a line along which the greatest forces occur during operation of the part. Such a gradient can be generated by radiation action on a tightly limited region of the part, for example by punctiform radiation action. The location of the radiation action is also selected dependent on the part geometry and, for example, can lie in the proximity of a stability-conditioned weak point of the component part. It is also possible to distribute the radiation action over a larger area of the part. Given rotationally symmetrically shaped parts, for example, it is possible to generate an annular heated zone, whereby a radial temperature distribution or a temperature gradient dropping radially toward the center of the rotation is generated.

DESCRIPTION OF THE PREFERRED EMBODIMENTS

Figure 1:
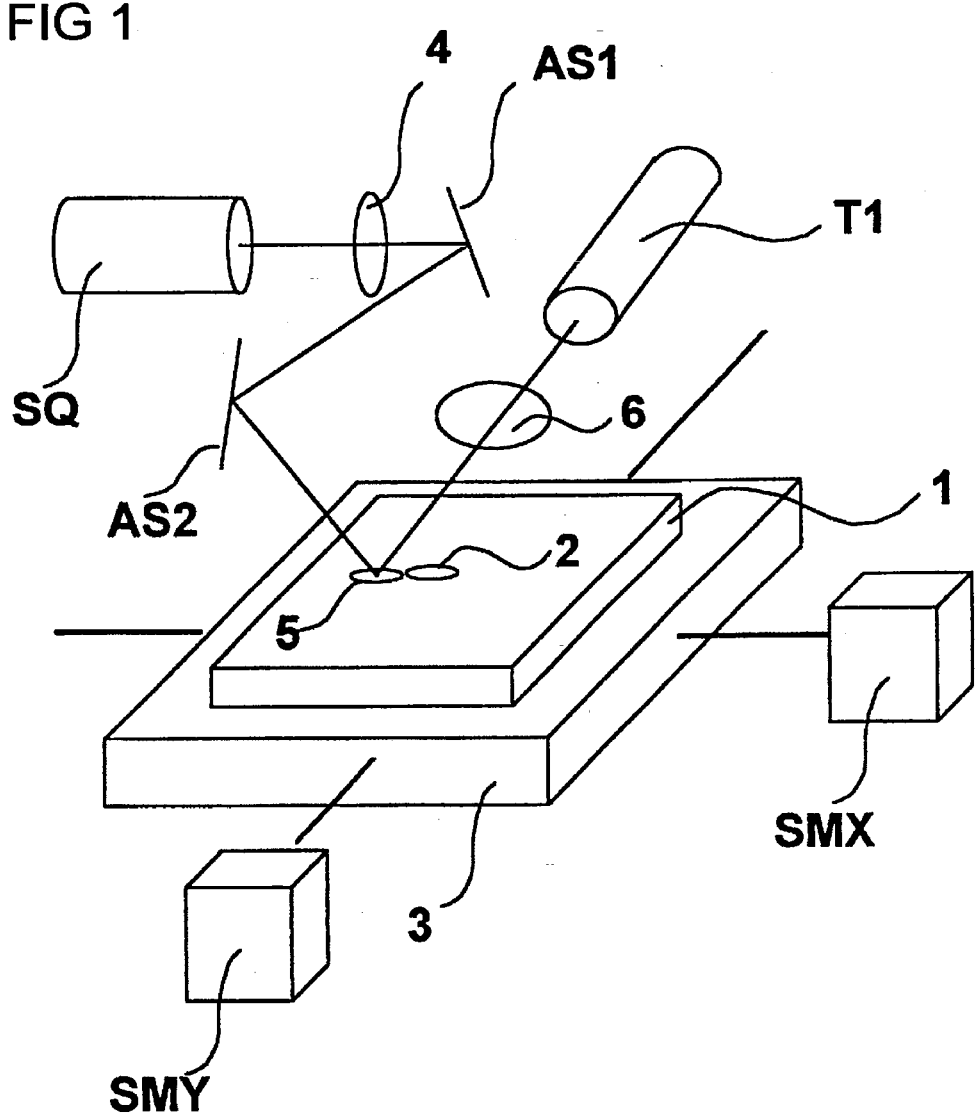
FIG. 1 shows an arrangement for the implementation of the method of the invention; and, FIG. 2 shows the method of the invention as a block circuit diagram.

FIG. 1 shows how the overload test of a ceramic heat shield should be implemented in the method of the invention. A quadratic plate 1 having a 200 mm edge length and a thickness of 5 mm serves as a model for a heat shield. The plate 1 is implemented, for example, of silicon nitride or silicon carbide. A bore 2 having a diameter of 20 mm is located in the middle of the plate 1 for fastening purposes.

The plate is arranged on a plane table 3. Two stepping motors SMX and SMY enable a translation of the plane table along the X-axis and the Y-axis.

A laser, for example a Nd:YAG laser, serves as radiation source SQ. As a result of its wavelength of approximately 1.06 μm, this is especially suited for non-oxidic ceramic and produces the required, high radiation capacity with which a fast energy infeed is possible. The further advantage of the solid state laser is the possibility opened up by its wavelength of implementing the optics 4 that serves the purpose of radiation bundling and radiation guidance of glass.

A first and a second deflection mirror AS1 or AS2, each of which can be respectively rotated around an axis, with the two axes preferably perpendicular relative to one another, serve the purpose of deflecting the laser beam. With the assistance of the optics 4 and of the deflection mirrors AS, the beam generated by the laser SQ is directed onto the part 1 where it generates a hot spot having a diameter of approximately 10 mm. Since the most critical location with respect to the mechanical stability of the part 1 lies close to the bore 2, the spot is likewise directed onto the plate 1 at a spacing of approximately 5 mm from the bore 2.

For monitoring the temperature distribution, which comprises at least one temperature gradient directed radially relative to the bore 2 in the present case, at least two temperature sensors T1 and T2 are required, only one thereof being shown in the FIG. for the sake of clarity. More temperature sensors can be required for more exact measurements of the temperature distribution.

A semiconductor component that utilizes the photoeffect can be employed as a temperature sensor T1, for example a photodiode that is sensitive in the infrared range. The temperature can be measured to a precision of ±5° C. in a simple way with the sensor. A time resolution of the temperature sensor of 10 msec is adequate for the part 1 employed in the exemplary embodiment. Given smaller parts having lower heat capacity, a faster identification of the temperature distribution is required, so that a single measurement of a temperature sensor T must occur, for example, within 800μsec. The topical precision of the temperature measurement is designed such that, for example, a temperature gradient of 300k/mm can be determined. Since the temperature measurement occurs in an "optical" way, it can be improved with a suitable optics 6. The measuring method also allows an adequate measuring spacing of the temperature sensor T from the part 1 which, for example, can amount to 15–23 cm. Larger measuring spacings that are advantageous for the method should also be possible with suitably selected temperature sensors given the same measuring position.

Figure 2:
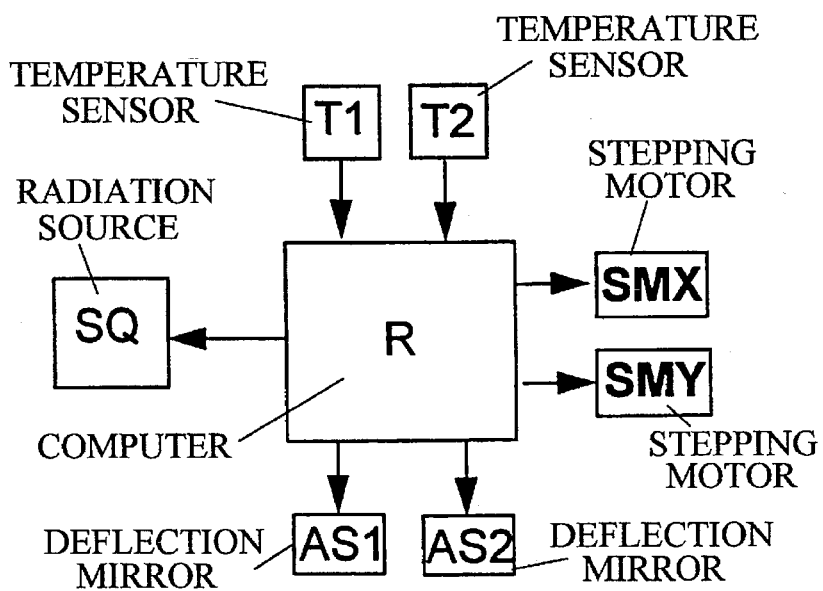

FIG. 2 explains the implementation of the method with reference to a schematic block diagram. A test stress that is required or desired for the method is calculated according to the finite element method. Taking the material properties and the conditions occurring during operation—which, for example, are mechanical stresses or, preferably, thermally induced stresses—, a temperature distribution that generates this test stress is calculated for the part 1. The monitoring of the temperature distribution occurs with reference to points typical of the specific temperature distribution.

The temperature distribution to be determined at the measuring points is input into a computer R employed for controlling the method. The temperature values identified by the temperature sensors T1, T2 . . . Tn are forwarded to the computer in a predetermined measuring frequency of, for example, 100 Hz, and are compared therein to the predetermined or desired values. Deviations from the desired value can occur by alignment of the laser beam via the deflection mirrors AS1 and AS2 that are likewise controlled by the computer R. Greater topical deviations can also be adjusted by the stepping motors SMX and SMY. Further, the temperature distribution can occur via the regulation of the power of the radiation source SQ, whereby more or less power is coupled into the spot 5 on the part 1 as warranted.

The sound emissions arising during the application of the test load in the case of crack growth are registered by an applied ultrasound sensor. The acoustic signals serve the purpose of documenting the part failure due to the test load.

When the desired temperature distribution and the overload stress (test stress) produced thereby have been achieved, the part 1 can be cooled, potentially by active cooling.

In order to do justice to all use conditions of the part 1, the procedure is now repeated, whereby a different temperature distribution and thus a differently directed test stress are produced in the part 1. In the selected exemplary embodiment, a further stationary punctiform radiation action onto a location in the proximity of the bore 5 is thereby suitable.

Overall, 8–10 hot spots are generated on the part by multiple repetition of the method with intervening cooling according to a pre-calculated test stress or temperature distribution. Given the indicated number of measuring points, for example, the method is ended after about 5–15 minutes given employment of an 800 watt solid state laser. The time required is correspondingly reduced, given a higher laser power.

After the implementation of the method, the part 1 is optically checked for damage such as, for example, the formation of cracks, and is potentially eliminated. Undamaged parts now only contain cracks below a specific crack length that is determined by the desired service life of the part under intended operating conditions. In addition to the exemplary embodiment recited by way of example, the test method of the invention is also suitable as a proof test for arbitrarily shaped ceramic parts, whereby temperature distributions other than those recited can be respectively generated on the part. Arbitrary test stresses can thus be simulated.

Although various minor changes and modifications might be proposed by those skilled in the art, it will be understood that I wish to include within the claims of the patent warranted hereon all such changes and modifications as reasonably come within my contribution to the art.

We claim as our invention:

1. A method for testing a structural ceramic part by creating a thermally induced test stress, comprising the steps of:

calculating a desired temperature distribution which induces at least an amount of stress the part must withstand during use;

creating a temperature distribution by heating the part by radiation action in predetermined regions;

measuring the created temperature distribution of the part by topically resolving temperature sensors;

comparing the measured temperature distribution of the part to the calculated, desired temperature distribution;

regulating at least one of duration and location of the radiation action until the desired temperature distribution has been produced in the part; and detecting a failure of the part by sound emission analysis, and eliminating the part if damaged.

2. A method according to claim 1 wherein the radiation action occurs via a laser.

3. A method according to claim 1 wherein the part is additionally actively cooled for producing the desired temperature distribution.

4. A method according to claim 1 wherein the measured temperature distribution is identified with semiconductor sensors arranged at a spacing from the part by use of photoeffect.

5. A method according to claim 1 wherein the part is cooled after a first temperature distribution has been generated, and wherein at least one further temperature distribution differing from the first temperature distribution is subsequently produced in an analogous way.

6. A method according to claim 1 wherein a test stress is generated in the part via the temperature distribution which corresponds in magnitude to a thermally mechanical stress occurring in a later, intended employment of the structural ceramic part.

7. A method according to claims 1 wherein the radiation action occurs via a laser, and a relative motion between the part and the laser is implemented during the radiation action.

8. A method according to claim 7 wherein the relative motion is implemented with a stepping motor.

9. A method according to claim 1 wherein the part is an element selected from the group consisting of a valve, a heat shield, a combustion chamber lining, and a turbine paddle.

10. A method for testing a structural ceramic part by creating a thermally induced test stress, comprising the steps of:

calculating a desired temperature distribution which induces at least an amount of stress the part must withstand during use;

creating a temperature distribution by heating the part by radiation with a laser beam in predetermined regions;

measuring the created temperature distribution by measuring temperatures at different locations on the part by use of a plurality of temperature sensors;

comparing the measured temperature distribution to the calculated temperature distribution;

regulating at least one of duration and location of the radiation until the desired temperature distribution has been produced in the part; and detecting a failure of the part, and eliminating the part if damaged.

* * * * *